United States Patent [19]

McCullough et al.

[11] Patent Number: 4,776,357

[45] Date of Patent: Oct. 11, 1988

[54] DENTAL FLOSS APPLICATOR

[76] Inventors: Edward E. McCullough; Kevin W. McGaha, both of P.O. Box 46, Brigham City, Utah 84302

[21] Appl. No.: 90,115

[22] Filed: Aug. 27, 1987

[51] Int. Cl.$^4$ ............................................. A61C 15/00
[52] U.S. Cl. ................................................... 132/327
[58] Field of Search ................. 433/124; 132/89, 90, 132/91, 92 R, 92 A

[56] References Cited

U.S. PATENT DOCUMENTS 1,815,408  7/1931  Jordan .................................... 132/91

*Primary Examiner*—Robert Peshock
*Attorney, Agent, or Firm*—Edward E. McCullough

[57] ABSTRACT

A dental floss applicator is especially designed to cooperate with a floss-loading device. It has a pair of resilient, juxtaposed, divergent prongs attached to a handle. Slots in the ends of the prongs enable the applicator to hold floss of the type having rigid nodules fixed to it at spaced-apart intervals. These intervals are somewhat shorter than the relaxed distance between the prongs, so that the prongs bear outwardly against a pair of nodules. A small outwardly-extending shoulder on the end of each prongs serves the purpose of: (1) Trapping a nodule of the floss, so that a span of the floss is firmly retained thereby; (2) Bearing against convergent surfaces of the loading device, by means of which the prongs are compressed toward each other for loading floss thereon; and (3) It is a device whereby the prongs are retained between the convergent surfaces of the loading device (these convergent surfaces have longitudinal, inwardly-extending lips or flanges under which the shoulders of the prongs slide).

7 Claims, 1 Drawing Sheet

U.S. Patent    Oct. 11, 1988    4,776,357
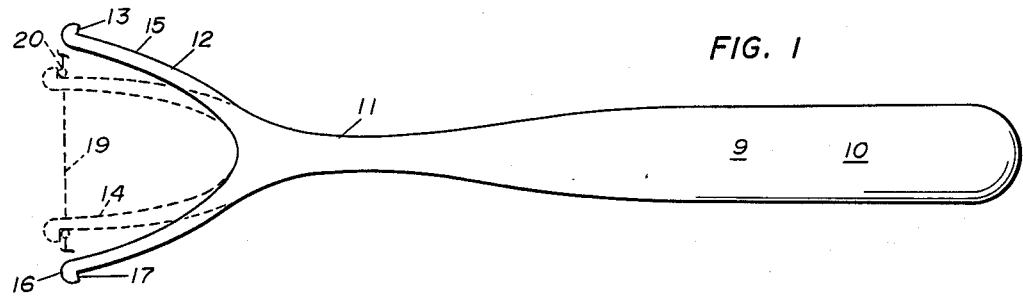
FIG. 1
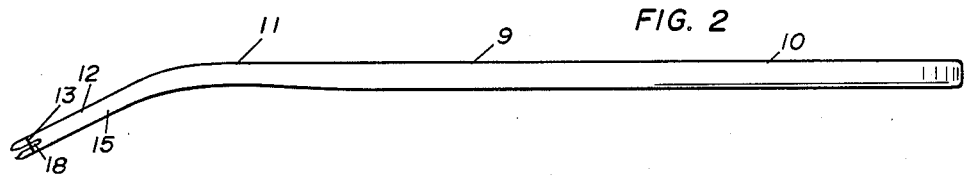
FIG. 2
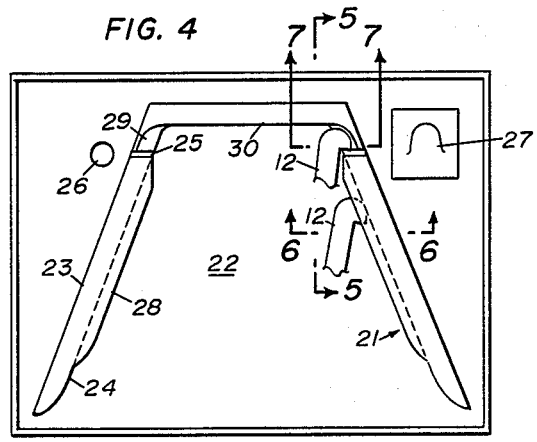
FIG. 4
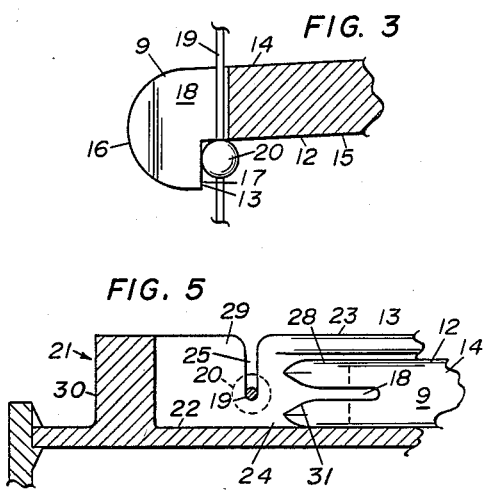
FIG. 3
FIG. 5
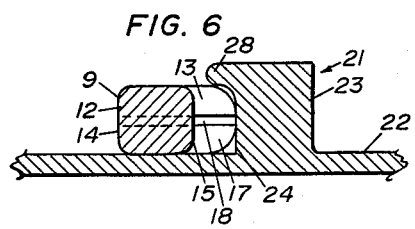
FIG. 6
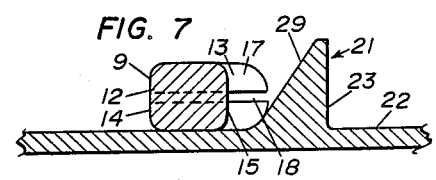
FIG. 7

DENTAL FLOSS APPLICATOR

CROSS REFERENCES TO RELATED APPLICATIONS

This application is related to the following applications for patent filed simultaneously herewith: "Method and Apparatus for a Dental Floss System" by Edward E. McCullough and Kevin W. McGaha, Ser. No. 07/090116, filed Aug. 27, 1987, now U.S. Pat. No. 4,753,254 issued 6/28/88; and "Dental Floss Applicator" (for design patent) by Edward E. McCullough, Ser. No. 07/090,139, filed Aug. 27, 1987.

BACKGROUND OF THE INVENTION

1. Field of the Invention

This invention relates to applicators for applying dental floss to the teeth of a user. More specifically, it pertains to dental floss applicators of the type having a pair of resilient, slotted prongs for use with dental floss having nodules fixed thereto at intervals, such that the nodules can be used for retaining the floss in the slots of the prongs; and especially to such applicators adapted for use with apparatus of the type described herein, and in the first related application cited above, for loading dental floss into the prongs of the applicator.

2. Description of the Prior Art

Dental floss having nodules fixed thereto at intervals is known in the prior art, as are applicators having resilient, slotted prongs for holding the floss by bearing outwardly against two adjacent nodules on the floss. Examples of such systems are shown in U.S. Pat. Nos. 1,815,408 "Dental Floss Holder" to J. K. Jordan, and 3,631,869 "Dental Floss Holder" to R. J. Espinosa. A similar device is shown in U.S. Pat. No. 4,162,687 "Dental Flossing Device" to L. G. Lorch. In this patent, the flossing material is made in short segments, each of which has a small, circular grommet that fits over a knob at the end of each prong of the applicator. German Pat. No. 1095460 to Gustav Frantz is also somewhat similar to the first two patents cited above. However, in this patent, tension on a segment of floss is achieved by a collar surrounding both prongs at a point at which they are disposed at and angle to one another, so that, by sliding the collar along the prongs, they can be positioned at a desired distance from one another.

Other U.S. Patents, known to the applicant, that show dental-floss holders, but which are fairly unrelated to the present invention are: U.S. Pat. Nos. 4,253,477; 3,828,804; 2,702,555; 3,974,842; and 4,052,994.

None of the applicators taught in these prior-art patents have the appropriate configuration to function successfully in cooperation with a preferred embodiment of the floss-loading device of the cited, related patent application.

This device essentially comprises two elongated, juxtaposed, convergent surfaces fixed perpendicular to a third surface. The floss is supported in a slot in each convergent surface, so that it extends from one surface to the other at a point where the distance between the surfaces is less that the distance between nodules on the floss. The convergent surfaces are equipped, at their upper edges, with inwardly-extending lips between their divergent ends and the slots for retention of the prongs of the applicator, and means near the convergent end of the convergent surfaces for automatically ejecting the prongs of the applicator when they have been loaded with floss. The user places the prongs of the applicator between the divergent ends of the convergent surfaces and moves them toward the floss until it is grasped in the slots of the prongs. The prongs are then freed from between the convergent surfaces and ejected therefrom by upwardly-divergent surfaces between the slots and the convergent ends of the otherwise convergent surfaces. Neither of the embodiments taught in the patent to Jordan would be freed from the lips on the convergent surfaces of the loading device after the floss has been grasped in the slots of the applicator. Also, the first embodiment could not function with the ejection means of the floss-loading device; and the second embodiment does not have the slots in its prongs oriented properly for grasping the floss supported in the convergent surfaces. For similar reasons, the applicators taught in the Patents to Espinosa and Frantz would not function in cooperation with the cited floss-loading device.

SUMMARY OF THE INVENTION

A difficulty experienced when using dental-floss systems of the type described in U.S. Pat. No. 1,815,408 to Jordan is that loading the floss material onto the applicator is somewhat awkward. Ideally, the user must have three hands—one for holding the floss supply, one for holding the applicator and compressing its prongs together, and a third for loading a segment of floss onto the prongs of the applicator. While most normal adults should be able to learn to juggle such devices effectively, it can be a problem for children and for individuals with impaired manual skills, e.g. arthritic hands. Of course, not having to acquire special skills in order to operate a simple device is appreciated by everyone.

The present invention is directed primarily toward overcoming this difficulty in the prior art. Therefore, it is a primary object of the invention to provide a dental floss applicator that can function in cooperation with a floss-loading device of the type described above and shown in the accompanying drawings. Another object of the invention is to provide a dental floss applicator that is simple in construction; and, therefore, reliable and easily cleaned.

The applicator of the invention has a handle and two, juxtaposed, resilient prongs fixed thereto. Each prongs has a slot in its end for grasping dental floss; and an outwardly-extending shoulder that performs the several functions of (1) trapping a nodule of the floss so that it cannot escape from the prong of the applicator, (2) bearing against the convergent surfaces of the floss-loading device, (3) serving as a means for retaining the pronge of the applicator by the inwardly-extending lips on the convergent surfaces of the floss-loading device, and (4) bearing against the ejection surfaces of the floss-loading device when the floss therein has been grasped by the prongs of the applicator.

Other objects and advantages of the invention will be noted as the following, detailed description is read with reference to the accompanying drawings. Each part number refers to the same part throughout the disclosure.

BRIEF DESCRIPTION OF THE DRAWINGS

In the drawings:

FIG. 1 is a top view of the invention, with the prongs shown in the same plane as the handle;

FIG. 2 is a side view of FIG. 1, but showing the prongs curved out of the plane of the handle;

FIG. 3 is a greatly-enlarged sectional view of the end portion of the lower prong of the invention, as it appears in FIG. 1;

FIG. 4 is a top view of the cited floss-loading device, showing how the prongs of the invention cooperate therewith;

FIG. 5 is an enlarged, fragmentary section taken on line 5—5 of FIG. 4 to show the relationships of the applicator, the loading device, and the floss (but showing only one prong);

FIG. 6 is an enlarged, fragmentary section taken on line 6—6 of FIG. 4; and

FIG. 7 is an enlarged, fragmentary section taken on line 7—7 of FIG. 4.

DESCRIPTION OF THE PREFERRED EMBODIMENTS

The applicator 9 of the invention, as best shown in FIGS. 1 and 2, has a handle 10 that narrows to a shank 11, to which two, juxtaposed, resilient prongs 12 are integrally fixed. The prongs 12 diverge outwardly from the shank 11 and the end of each has a small shoulder 13 that extends outwardly, relative to the central, longitudinal axis of the applicator 9.

As shown in FIG. 3, each shoulder 13 is preferably formed by rounding the end of each prong 12 with a continuous curve that is tangent to the inner surface 14 of the prong and extends beyond the outer surface 15 thereof, forming an approximate 180 degree arc 16. The outer end of this arc 16 and the outer surface 15 of the prong 12 are then joined by a flat surfacce 17 that is approximately perpendicular to the portion of the prong 12 of which the shoulder 13 is a part. The outer edge of the shoulder 13 thus formed is the outermost point of the applicator 9, relative to the central, longitudinal axis thereof.

A slot 18 that lies in the plane of the prongs 12 passes through the end of each prong 12, preferably extending a short distance inward of the flat surface 17; so that dental floss 19, when fully loaded into the slot 18, will lie slightly inward of the surface 17. At the end portions of each prong 12, the slots 18 are flared or outwardly-divergent 31 to facilitate the interception of floss therein (See FIG. 5).

It is optional as to whether the prongs 12 are made of the same material as the handle 10 of the applicator 9. The handle can obviously be made of any rigid material that will support the prongs, and it could be fastened to the prongs in any number of well-known ways, such as by bonding, mechanical press fitting, etc. The prongs can be made of any strong, nontoxic, resilient material, such as stainless spring steel, polypropylene, nylon, etc.

The type of dental floss 19 that is used by the invention is known in the art, as stated above. The floss, itself, can be any of the commonly-used varieties, but has rigid nodules 20 fixed to it as intervals that define "functional spans" of floss (See FIGS. 1 and 3).

For convenience and clarity in the following description and claims: "Functional pair" shall refer to two adjacent nodules 20 on the floss 19 that define the appropriate length of floss that can be loaded onto the applicator 9 effectively (i.e. a span somewhat shorter than the relaxed distance between the prongs 12); and "Functional span" shall refer to the length of floss 19 between two functional pairs of nodules 20.

The loading device 21, with which the present invention is intended to cooperate, is built on a flat surface 22, which is preferably the top surface of a dental-floss container, not shown (See FIGS. 5 and 6). The loading device 21 essentially comprises a pair of elongated, juxtaposed, convergent members 23 that are fixed to the surface 22. Their inner, opposing surfaces 24 are preferably perpendicular to the flat surface 22. Each convergent member 23 has a slot 25 that extends from its upper edge perpendicular to the surface 22 to a point near that surface. The slots 25 are located in the members 23 at positions where the distance between them is somewhat less than a functional span of the floss. An opening 26 in the surface 22 permits passage of floss therethrough from a supply of floss within the container. This opening 26 is located on one side of the pair of slots 25 and a cutting tab 27 is fixed to the surface 22 opposite the opening 26 on the other side of the slots 25.

A preferred form of the invention includes a small, inwardly projecting lip 28 at the upper edge of each elongated member 23 that extends from its divergent end to its slot 25 (See FIGS. 4, 5 and 6). This feature retains the shoulders 13 of the applicator prongs between the convergent surfaces 24 during the forward motion of the prongs 12 toward the supported span of floss 19, to insure that the floss 19 is grasped in the slots 18 of the applicator 9.

Also, the portion 29 of each elongated surface 24 between its slot 25 and its convergent end is upwardly divergent and curved to conform to the approximate shape of the end portions of the prongs 12 (See FIGS. 4, 5, and 7). This feature allows the prongs 12 to spring outwardly and automatically eject upwardly from between the elongated surfaces 24 when the floss 19 has been loaded into the applicator prongs.

When practicing the invention, the user first pulls a length of floss 19 containing two functional nodules 20 through the opening 26. This floss is then placed in the slots 25 in the elongated members 23 so that each of the nodules 20 rests on the outside surface of its respective member 23. He then places the shoulders 13 of the prongs 12 between the divergent ends of the convergent surfaces 24, under the lips 28 and in contact with the upper surface 22 of the container, so that the slots 18 in the prongs 12 are substantially parallel to the surface 22 (See FIGS. 5 and 6). Maintaining this attitude, the prongs 12 are then compressed toward each other by moving them forwardly toward the convergent ends of the surfaces 24 until stopped by the stop member 30, which is a small plate fixed to the convergent ends of the elongated members 23 and perpendicular to the flat surface 22. At this point, the span of floss 19 supported in the slots 25 has been fully passed into the slots 18 in the ends of the prongs 12. The shoulders 13 of the prongs 12 then bear outwardly against the upwardly divergent surfaces 29 (See FIG. 7), simultaneously ejecting the prongs from between the convergent surfaces 24 and trapping each of the nodules 19 behind its respective shoulder 13.

By moving the applicator 9 slightly a further length of floss 19 containing a second set of functional nodules 20 is pulled through the opening 26. This second functional span of floss 19 is loaded into the slots 25 in the same manner as was the first span—with the nodules 20 being placed outside the elongated members 23. By another slight movement of the applicator 9, the floss 9 is passed under the cutting tab 27 and severed. The loaded span of floss is then applied to the teeth of the user by means of the applicator 9. When the user is ready for a second span of the floss 19, the prongs 12 are compressed together manually, the used floss removed, and the above procedure for loading the floss 19 is repeated.

An invention has been described that advances the art of dental hygiene. Although the embodiments thereof have been described in considerable detail, it should be noted that many such details may be altered without departing from the scope of the invention, as it is defined in the following claims.

What is claimed is:

1. A dental floss applicator for use with floss having modules fixed thereto at intervals and with a floss-loading device having two, juxtaposed, elongated surfaces, having inwardly-extending lips on their upper edges, fixed perpendicularly to a third surface at their lower edges so that they converge tpward a span of the floss supported to extend from one convergent surface to the other, said applicator comprising:
   a handle;
   two resilient, juxtaposed prongs, each attached at one end to said handle;
   a single, outwardly-extending shoulder on the end portion of each prong that extends farther outwardly from the central, longitudinal axis of the applicator than any other portion of the prong so that it can bear against one of the convergent surfaces beneath the lip thereon; and
   means for grasping floss in said prongs.

2. The applicator of claim 1 wherein said means for grasping floss is structure defining a slot in the end portion of each of said prongs.

3. The applicator of claim 2 wherein said slot extends through each shoulder and lies in the plane of the prongs.

4. The applicator of claim 3 wherein said slots are outwardly flared at the ends of the prongs to enhance their ability to grasp dental floss.

5. The applicator of claim 3 wherein each of said slots extends inwardly toward said handle and slightly beyond its corresponding shoulder for assured retention of said floss by trapping a nodule thereof behind each of said shoulders.

6. The applicator of claim 1 wherein the end portions of said prongs are curved out of the plane of the remainder of the applicator.

7. The applicator of claim 1 wherein said shoulder has a curved surface that comprises a continuation of the inner surface of its corresponding prong, said curved surface describing substantially a semicircle curving around the end of the prong and extending laterally beyond the outer surface of said prong; and a flat surface substantially perpendicular to said prong that extends outwardly from the outer surface of the prong near the end portin thereof, said flat surface joining, at its outer edge, the outer end of said curved surface.

* * * * *